(12) United States Patent
Miki et al.

(10) Patent No.: US 11,767,371 B2
(45) Date of Patent: Sep. 26, 2023

(54) HYDROXYPROPYL METHYL CELLULOSE ACETATE SUCCINATE, METHOD FOR PRODUCING THE SAME, AND COMPOSITION FOR HOT-MELT EXTRUSION

(71) Applicant: Shin-Etsu Chemical Co., Ltd., Tokyo (JP)

(72) Inventors: Akiko Miki, Tokyo (JP); Taishi Kitaguchi, Niigata (JP); Akira Kitamura, Niigata (JP); Mitsuo Narita, Niigata (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 96 days.

(21) Appl. No.: 17/484,405

(22) Filed: Sep. 24, 2021

(65) Prior Publication Data
US 2022/0106410 A1    Apr. 7, 2022

(30) Foreign Application Priority Data
Oct. 1, 2020    (JP) ................. 2020-166785

(51) Int. Cl.
| | | |
|---|---|---|
| *C08B 3/16* | (2006.01) | |
| *C08B 13/00* | (2006.01) | |
| *B29C 48/00* | (2019.01) | |
| *B29C 48/36* | (2019.01) | |
| *C08L 1/32* | (2006.01) | |
| *A61K 45/06* | (2006.01) | |
| *A61K 47/38* | (2006.01) | |
| *B29K 1/00* | (2006.01) | |

(52) U.S. Cl.
CPC .............. *C08B 3/16* (2013.01); *B29C 48/022* (2019.02); *B29C 48/36* (2019.02); *C08B 13/00* (2013.01); *C08L 1/32* (2013.01); *A61K 45/06* (2013.01); *A61K 47/38* (2013.01); *B29K 2001/08* (2013.01)

(58) Field of Classification Search
CPC .................................. C08B 13/00; C08L 1/32
See application file for complete search history.

(56) References Cited

FOREIGN PATENT DOCUMENTS

| | | |
|---|---|---|
| EP | 3308775 A1 | 4/2018 |
| JP | H05339301 A | 12/1993 |
| WO | 2016069338 A1 | 5/2016 |

OTHER PUBLICATIONS

Patil et al., J. Water Pollut. Purif. Res., 2014, 1(2), p. 13-18. (Year: 2014).*
U.S. Appl. No. 17/448,771, filed Sep. 24, 2021, Miki et al.
Extended European Search Report corresponding to European Patent Application No. 21200304.0 (6 pages) (dated Feb. 21, 2022).

* cited by examiner

*Primary Examiner* — Jonathan S Lau
(74) *Attorney, Agent, or Firm* — Myers Bigel, P.A.

(57) ABSTRACT

There is provided a method for efficiently produce hydroxypropyl methyl cellulose acetate succinate (HPMCAS) having excellent flowability, where acetic acid in a reaction product mixture subjected to a wash and recovery step can be reduced. More specifically, there is provided a method for producing HPMCAS including an esterification step of esterifying hydroxypropyl methyl cellulose (HPMC) with acetic anhydride and succinic anhydride in acetic acid as a solvent to obtain a reaction product solution containing HPMCAS; a water addition step of adding water to the reaction product solution to obtain a water-added reaction product solution; an acetic acid removal step of removing at least a portion of both the solvent acetic acid and acetic acid derived from the acetic anhydride from the water-added reaction product solution to obtain a mixture having an acetic acid content reduced; and a wash and recovery step of washing the mixture and recovering the HPMCAS.

4 Claims, 1 Drawing Sheet

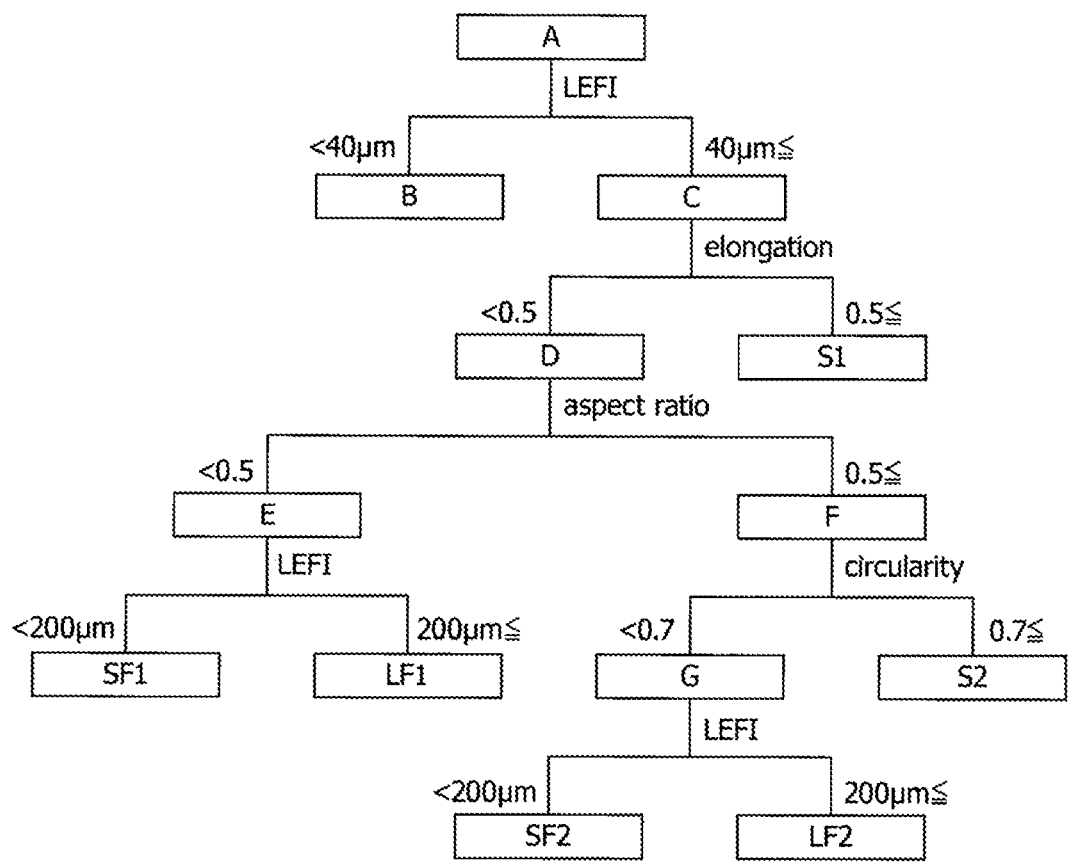

HYDROXYPROPYL METHYL CELLULOSE ACETATE SUCCINATE, METHOD FOR PRODUCING THE SAME, AND COMPOSITION FOR HOT-MELT EXTRUSION

BACKGROUND OF THE INVENTION

1. Field of the Invention

The invention relates to hydroxypropyl methyl cellulose acetate succinate, a method for producing the hydroxypropyl methyl cellulose acetate succinate, and a composition for hot-melt extrusion.

2. Related Art

Hydroxypropyl methyl cellulose acetate succinate (hereinafter also referred to as "HPMCAS") is a cellulose derivative having methoxy groups ($-OCH_3$), hydroxypropoxy groups ($-OC_3H_6OH$), acetyl groups ($-COCH_3$) and succinyl groups ($-COC_2H_4COOH$), and is produced by chemically modifying a cellulose.

HPMCAS is used as an enteric polymeric base material in a coating application, or as a solid dispersion containing a poorly water-soluble drug, and thus widely used particularly in the pharmaceutical field.

Examples of the method for producing HPMCAS include a method for producing a carboxyate-containing cellulose derivative, comprising a step of esterifying a cellulose with a polyvalent carboxylic anhydride in acetic acid as a solvent in the presence of an alkali metal carboxylate salt as a catalyst, while stirring by a biaxial stirrer, wherein an amount of the acetic acid as a solvent is 1 to 2 times the weight of the cellulose (JPH05-0339301A).

SUMMARY OF THE INVENTION

In a conventional method for producing HPMCAS such as that in JPH5-339301A, water is added to a reaction product solution to obtain a suspension having HPMCAS precipitated, and the HPMCAS in the suspension is washed with water to remove impurities. The suspension contains a large amount of acetic acid used as a solvent during the esterification step. Acetic acid contained in the water used for washing is discarded together with the water because of difficulty in recovery. However, the acetic acid is a factor of increasing the chemical oxygen demand (COD) of waste water. The acetic acid is also a factor of lowering the pH of waste water. The acetic acid is further a factor of odor.

Accordingly, after a suspension containing a large amount of acetic acid is subjected to a washing and recovering step, it is necessary to subject the water used for washing to waste water treatment such as biological treatment. An amount of acetic acid in the mixture subjected to the washing and recovering step is desirably small to reduce the load of the waste water treatment.

To reduce acetic acid in the mixture subjected to the washing and recovering step, it is considered to reduce the amount of acetic acid to be used in the esterification step. However, as described in JPH05-339301A, the reduction of the amount of acetic acid may make it difficult to uniformly dissolve the cellulose in an acetic acid solvent at a high concentration.

As described above, there is room for improvement in the conventional method for producing HPMCAS. There is also room for improvement of flowability of the conventional HPMCAS with respect to a flowability problem such as clogging in a hopper and a sanitary problem caused by HPMCAS remaining inside the hopper and pipe.

As a result of extensive studies to solve the above problems, the inventors have found that removal of acetic acid from a reaction product solution containing HPMCAS can reduce acetic acid in a mixture subjected to the wash and recovery step, and efficiently produce HPMCAS having excellent flowability, and thus have completed the invention.

In one aspect of the invention, there is provided a method for producing hydroxypropyl methyl cellulose acetate succinate, the method comprising:

an esterification step of esterifying hydroxypropyl methyl cellulose with acetic anhydride and succinic anhydride in acetic acid as a solvent to obtain a reaction product solution containing hydroxypropyl methyl cellulose acetate succinate;

a water addition step of adding water to the reaction product solution to obtain a water-added reaction product solution;

an acetic acid removal step of removing at least a portion of both the solvent acetic acid and acetic acid derived from the acetic anhydride from the water-added reaction product solution to obtain a mixture having an acetic acid content reduced; and a wash and recovery step of washing the mixture and recovering the hydroxypropyl methyl cellulose acetate succinate.

In another aspect of the invention, there is provided hydroxypropyl methyl cellulose acetate succinate having a volume fraction of spherical particles of 65.0% or more relative to all of hydroxypropyl methyl cellulose acetate succinate particles, the all of hydroxypropyl methyl cellulose acetate succinate, being classified, on a basis of dynamic image analysis, into fine particles, the spherical particles and fibrous particles, wherein the fine particles have a length of fiber of less than 40 µm;

the spherical particles have a length of fiber of 40 µm or more and consist of first and second spherical particles, wherein the first spherical particles have an elongation, which is a ratio of a diameter of fiber to a length of fiber, of 0.5 or more, and the second spherical particles have an elongation of less than 0.5, an aspect ratio, which is a ratio of a minimum Feret diameter to a maximum Feret diameter, of 0.5 or more, and a circularity, which is a ratio of a perimeter ($P_{EQPC}$) of a circle that has the same area as a projection area of a particle to a real perimeter ($P_{real}$) of a particle, of 0.7 or more;

the fibrous particles consist of long and short fibrous particles;

the long fibrous particles have a length of fiber of 200 µm or more and an elongation of less than 0.5, and consist of first and second long fibrous particles, wherein the first long fibrous particles have an aspect ratio of less than 0.5, and the second long fibrous particles have an aspect ratio of 0.5 or more and a circularity of less than 0.7; and the short fibrous particles have a length of fiber of 40 µm or more and less than 200 µm and an elongation of less than 0.5, and consist of first and second short fibrous particles, wherein the first short fibrous particles have an aspect ratio of less than 0.5, and the second short fibrous particles have an aspect ratio of 0.5 or more and a circularity of less than 0.7.

According to the invention, since at least a portion of acetic acid is removed from the reaction product solution containing HPMCAS, the amount of acetic acid in the mixture to be subjected to the wash and recover step can be reduced. For this reason, the burden in the waste water treatment is expected to be reduced, and the cost can be reduced by reusing the removed acetic acid.

In addition, HPMCAS having excellent flowability can be produced. For this reason, the mixing uniformity of HPMCAS and a drug in the composition for hot-melt extrusion can be improved, and the bridge formation by the mixed powder of HPMCAS and a drug in a hopper can be reduced. The uniformity of the drug content, the improvement of the mass ratio of HPMCAS to the drug, the quantitative supply and continuous operation can be expected.

BRIEF DESCRIPTION OF THE DRAWINGS

FIG. 1 shows a flow chart of dividing "all particles" of HPMCAS into four types of particles: "fine particles", "long fibrous particles (LF1 and LF2)", "short fibrous particles (SF1 and SF2)" and "spherical particles (S1 and S2)".

DETAILED DESCRIPTION OF THE PREFERRED EMBODIMENTS

Regarding the method for producing HPMCAS, there will be described an esterification step of esterifying hydroxypropyl methyl cellulose with acetic anhydride and succinic anhydride in acetic acid as a solvent to obtain a reaction product solution containing HPMCAS.

Hydroxypropyl methyl cellulose (hereinafter also referred to as "HPMC") is a non-ionic water-soluble cellulose ether. HPMC synthesized by a known method, or commercially available HPMC may be used.

The DS of methoxy groups of HPMC is preferably from 1.10 to 2.20, more preferably from 1.30 to 2.10, still more preferably from 1.60 to 2.00, and particularly preferably from 1.80 to 2.00, from the viewpoint of HPMC providing the reduced number of undissolved fibers. The MS of hydroxypropoxy groups of HPMC is preferably from 0.10 to 1.00, more preferably from 0.10 to 0.80, still more preferably from 0.15 to 0.60, and particularly preferably from 0.20 to 0.50, from the viewpoint of HPMC providing the reduced number of undissolved fibers.

The DS of methoxy groups of HPMC represents the degree of substitution of methoxy groups and means the average number of methoxy groups per anhydroglucose unit. The MS of the hydroxypropoxy groups of HPMC represents a molar substitution of hydroxypropoxy groups, and means the average mole number of hydroxypropoxy groups per mol of anhydroglucose. The DS of the methoxy groups and the MS of the hydroxypropoxy groups of HPMC may be determined by conversion of the values obtained by the measurement in accordance with the Japanese Pharmacopoeia Seventeenth Edition.

The viscosity at 20° C. of the 2% by mass aqueous solution of HPMC is preferably from 1.0 to 30.0 mPa·s, more preferably from 2.0 to 20.0 mPa·s, from the viewpoint of kneadability in the esterification step. The viscosity at 20° C. of a 2% by mass aqueous solution of HPMC may be measured by using a Ubbelohde viscometer in accordance with the method described in the monograph "Hypromellose" of the Japanese Pharmacopoeia Seventeenth Edition.

An amount of the acetic acid to be used is preferably from 3.5 to 10.0 mol, more preferably from 4.5 to 7.0 mol, and still more preferably from 5.0 to 6.5 mol, relative to 1 mol of HPMC, from the viewpoint of dissolving HPMC and increasing the reaction rate.

An amount of the acetic anhydride to be used is not particularly limited as long as HPMCAS having the desired substitution degree is obtained. It is preferably from 0.2 to 3.0 mol, more preferably from 0.4 to 1.8 mol, relative to 1 mol of HPMC from the viewpoint of reaction efficiency.

An amount of the succinic anhydride to be used is not particularly limited as long as HPMCAS having the desired substitution degree is obtained. It is preferably from 0.1 to 1.5 mol, more preferably from 0.15 to 1.2 mol, relative to 1 mol of HPMC from the viewpoint of reaction efficiency.

The esterification reaction may be carried out in the presence of a catalyst. As the catalyst, an alkali metal carboxylate salt such as sodium acetate is preferred from the viewpoint of economy. The optional catalyst may be used singly or in combination of two or more. A commercially available catalyst may be used.

The amount of the optional catalyst to be used may be selected in consideration of the substitution degree of HPMCAS. It is preferably from 0.1 to 3.0 mol, more preferably from 0.3 to 2.0 mol, relative to 1 mol of HPMC from the viewpoint of reaction efficiency.

The esterification is preferably carried out using a kneader reactor or the like from the viewpoint of reaction efficiency. The reaction temperature in the esterification step is preferably from 60 to 120° C., more preferably from 60 to 100° C., from the viewpoint of the reaction rate. The reaction time in the esterification step is preferably from 2 to 8 hours, more preferably from 3 to 6 hours, from the viewpoint of obtaining HPMCAS having the desired substitution degrees.

Next, there is described a water addition step of adding water to the reaction product solution containing HPMCAS to obtain a water-added reaction product solution.

The water addition step allows unreacted acetic anhydride and succinic anhydride to be treated.

The water is added in such an amount as not to precipitate the HPMCAS from the viewpoint of preventing deterioration in transferability due to precipitation of HPMCAS. An amount of the water to be added is preferably not more than 200 parts by mass, more preferably from 2 to 180 parts by mass, and still more preferably from 5 to 130 parts by mass, relative to 100 parts by mass of the starting HPMC used in the esterification reaction. The temperature of the reaction product solution containing HPMCAS to be subjected to the addition of water is preferably from 60 to 100° C. from the viewpoint of carrying out the acetic acid removal step sequentially after adding the water.

Next, there will be described an acetic acid removal step of removing at least a portion of acetic acid from the water-added reaction product solution to obtain a mixture having the acetic acid content reduced. The acetic acid to be removed includes acetic acid used as a solvent, acetic acid which is a by-product in acetylation of HPMC with acetic anhydride, and acetic acid generated by hydrolyzing unreacted acetic anhydride in the water addition step. In terms of quantity, the acetic acid used as a solvent is mainly removed. When sodium acetate is used as a catalyst, it is at the following equilibrium, so that acetic acid derived from sodium acetate is not considered.

$$CH_3COONa + CH_3COOH = CH_3COOH + CH_3COONa$$

The method of removing at least a portion of acetic acid from the water-added reaction product solution is not particularly limited. The acetic acid removal step preferably comprises evaporating acetic acid by heating and stirring the water-added reaction product solution under a reduced pressure to recover the acetic acid from the viewpoint of efficiently removing and recovering acetic acid.

The acetic acid removal step may be carried out, for example, by using an apparatus capable of stirring a high viscosity water-added reaction product solution and ensuring a sealed state for heating and reduced pressure or for reduced pressure. Examples of the apparatus include a reactor being capable of heating and reducing an inside pressure and being equipped with a stirring blade that rotates; a reactor being capable of heating and reducing an inside pressure and being equipped with a stirring blade that rotates and orbitally revolves. The apparatus is preferably a reactor capable of heating and reducing an inside pressure, and being equipped with a stirring blade that rotates and orbitally revolves, and for example, a 5 L vertical kneader reactor (Trimix TX-5 produced by INOUE MFG., Inc.) having three frame-shaped stirring blades that rotate and orbitally revolve. The peripheral speed in the rotational motion of one stirring blade is preferably from 0.01 to 2.00 m/s from the viewpoint of uniformity of stirring in the acetic acid removal step. When the revolving motion is also used, the peripheral speed in the revolving motion of one stirring blade is preferably from 0.001 to 2.00 m/s. As used herein, the term "peripheral speed in the rotational motion" refers to the speed of the fastest part (i.e., the outermost periphery) of one stirring blade that rotates in the apparatus used. The "peripheral speed in the revolving motion" refers to the speed of the fastest part (i.e., the outermost periphery) of one stirring blade that orbitally revolves in the apparatus used.

The acetic acid removal temperature in the acetic acid removal step is preferably from 60 to 100° C. from the viewpoint of evaporation of acetic acid. The reduced pressure in the acetic acid removing step is preferably from −0.10 to −0.02 MPaG from the viewpoint of evaporation of acetic acid. The reduced pressure in the acetic acid removal step can be performed using an aspirator or the like.

The acetic acid removal time in the acetic acid removal step is preferably from 0.5 to 5 hours from the viewpoint of productivity.

The evaporated acetic acid may be recovered in a cooled trap or the like connected to the apparatus. The trap is preferably cooled by ice or the like. The recovered acetic acid may contain water.

The ratio of an amount of acetic acid removed in the acetic acid removal step to an amount of acetic acid added as a solvent is referred to as a removal percentage of acetic acid. The removal percentage of acetic acid is preferably 10.0% or more, more preferably from 25.0 to 99.9%, still more preferably from 40.0 to 99.9%, and particularly preferably from 88.0 to 99.8%, from the viewpoint of flowability of HPMCAS.

The removal percentage of acetic acid in the acetic acid removal step is defined by the following formula considering that the removed acetic acid is a mixture of acetic acid and the water added in the water addition step.

$$\text{Removal percentage(\%) of acetic acid} = \{(C \times D/100)/A\} \times 100$$

In the above formula, "A" means a mass ratio of acetic acid used as a solvent to a starting HPMC; "C" means a mass ratio of a recovered mixture containing acetic acid to a starting HPMC; and "D" means a concentration of acetic acid in the recovered mixture, wherein the recovered mixture also contains acetic acid derived from acetic anhydride and the water added in the water addition step.

The mixture having the acetic acid content reduced and being subjected to the wash and recovery step is preferably in a solid form from the viewpoint of flowability of HPMCAS. When the mixture having the acetic acid content reduced is in a liquid form having high viscosity, a solid mixture may be obtained by cooling the mixture in a liquid form to room temperature.

An optional pulverization step of pulverizing the mixture in a solid form may be carried out between the acetic acid removal step and the later-described wash and recovery step to obtain a pulverized mixture having the acetic acid content reduced from the viewpoint of efficiently washing a mixture having the acetic acid content reduced in a solid form.

The pulverization may be carried out by using a pulverizer. Examples of the pulverizer include a high-speed rotary pulverizer such as a hammer mill and a pin mill; a high shear apparatus such as a homogenizing mixer and a high shear mill; a roll-type pulverizer such as a roller mill; a pulverizer with the grinding media such as a vibration mill and a planetary mill; and a fluid-type pulverizer such as a jet mill.

When the mixture having the acetic acid content reduced is a solid having no stickiness, it may be pulverized as it is (i.e., dry pulverization). When the mixture having the acetic acid content reduced is a sticky solid, the mixture may be subjected to addition of water and then pulverized (i.e., wet pulverization). In general, when a mixture having the acetic acid content reduced is in a solid form, the stickiness becomes weaker as the removal percentage of acetic acid becomes higher and the acetic acid content becomes smaller. The temperature of the water to be added is preferably from 5 to 40° C. from the viewpoint of pulverization of HPMCAS. The amount of water to be added is preferably from 100 to 1000 parts by mass relative to 100 parts by mass of the mixture in a solid form having the acetic acid content reduced.

Next, there will be described a wash and recovery step of washing the mixture having the acetic acid reduced and recovering the hydroxypropyl methyl cellulose acetate succinate.

The method of wash and recovery is not particularly limited. Examples of the method include a method comprising steps of: mixing the mixture having the acetic acid content reduced with water to obtain a water-containing mixture, subjecting the water-containing mixture to centrifugation, filtration, decantation or the like to obtain crude HPMCAS, dispersing the crude HPMCAS in water for washing while stirring with a stirrer to obtain a dispersion, and subjecting the dispersion to centrifugation, filtration or the like to remove the water for washing; a method comprising a step of subjecting the mixture having the acetic acid content reduced or the crude HPMCAS to continuous flow of water; and a method comprising a step of repeatedly replacing a portion of the liquid in the water-containing mixture by water.

The water-containing mixture containing the mixture having the acetic acid content reduced and water is preferably a suspension from the viewpoint of washing.

The temperature of the water to be used for washing is preferably from 5 to 40° C. from the viewpoint of efficiently removing impurities contained in HPMCAS. An amount of the water to be used for washing varies depending on the washing method. For example, when crude HPMCAS obtained by centrifugation or filtration is washed, the amount of water to be used for washing is preferably 200 to 20000 parts by mass relative to 100 parts by mass of the mixture having the acetic acid content reduced from the viewpoint of obtaining HPMCAS with reduced impurities.

The amount of water to be used for washing may be preferably selected to fall within the above range in combination with the amount of water added in the water addition step.

The obtained HPMCAS may be optionally dried. The drying temperature is preferably from 40 to 100° C., more preferably from 40 to 80° C., from the viewpoint of preventing aggregation of HPMCAS. The drying time is preferably from 1 to 20 hours, more preferably from 3 to 15 hours, from the viewpoint of preventing aggregation of HPMCAS.

The obtained HPMCAS may be optionally subjected to sieving to obtain a desired average particle size.

The viscosity at 20° C. of a 2% by mass HPMCAS solution obtained by dissolving HPMCAS in a 0.43% by mass aqueous sodium hydroxide solution is preferably from 1.0 to 10.0 mPa·s, more preferably from 1.5 to 5.0 mPa·s. The viscosity at 20° C. of a 2% by mass HPMCAS solution obtained by dissolving HPMCAS in a 0.43% by mass aqueous sodium hydroxide solution may be measured by using an Ubbelohde viscometer in accordance with the method described in the monograph "Hypromellose Acetate Succinate" of the Japanese Pharmacopoeia Seventeenth Edition.

The DS of the methoxy groups of HPMCAS is preferably from 1.10 to 2.20, more preferably from 1.30 to 2.10, still more preferably from 1.60 to 2.00, and most preferably from 1.80 to 2.00.

The MS of the hydroxypropoxy groups of HPMCAS is preferably from 0.10 to 1.00, more preferably from 0.10 to 0.80, still more preferably from 0.15 to 0.60, and most preferably from 0.20 to 0.50.

The DS of the acetyl groups of HPMCAS is preferably from 0.10 to 2.50, more preferably from 0.10 to 1.00, and still more preferably from 0.20 to 0.80.

The DS of the succinyl groups of HPMCAS is preferably from 0.10 to 2.50, more preferably from 0.10 to 1.00, and still more preferably from 0.10 to 0.60.

The ratio of the DS of the acetyl groups to the DS of the succinyl groups of HPMCAS, the ratio (Ac/Suc), is preferably from 0.50 to 4.00, more preferably from 0.80 to 3.70, from the viewpoint of solubility.

The DS of the methoxy groups, the DS of the acetyl groups, the DS of the succinyl groups and the MS of the hydroxypropoxy groups of HPMCAS may be obtained by conversion of the values obtained in accordance with the method in the monograph "Hypromellose Acetate Succinate" of the Japanese Pharmacopoeia Seventeenth Edition. The DS of the methoxy groups, the acetyl groups or the succinyl groups of HPMCAS represents a degree of substitution, and means the average number of methoxy groups, acetyl groups, or succinyl groups per anhydroglucose unit. Further, MS of the hydroxypropoxy groups of HPMCAS represents a molar substitution, and means the average mole number of hydroxypropoxy groups per anhydroglucose unit.

The particle size $D_{50}$ at the cumulative 50% in the particle size distribution of HPMCAS may be appropriately selected depending on the application. It is preferably from 50 to 700 µm, more preferably from 100 to 600 µm, and still more preferably from 300 to 500 µm from the viewpoint of the flowability of HPMCAS.

The particle size ratio of $D_{90}$ to $D_{10}$, which is a ratio of the particle size at cumulative 90% to the particle size at cumulative 10% in the particle size distribution, is preferably 40.0 or less, more preferably from 0.5 to 10.0, and still more preferably from 1.0 to 4.0. The particle size ratio of $D_{90}$ to $D_{10}$ represents the width of the particle size distribution.

The $D_{10}$, $D_{50}$ and $D_{90}$ in the particle size distribution of HPMCAS may be measured at a dispersion pressure of 2 bars using a dry laser diffraction particle size distribution analyzer (Mastersizer 3000 produced by Malvern Panalytical Ltd.). The dry laser diffraction particle size distribution analyzer is a device for jetting a powder sample with compressed air, irradiating it with a laser beam, and measuring the diameter of the volume-equivalent sphere by the diffraction intensity. Examples thereof include Mastersizer produced by British Malvern Panalytical Ltd. and a HELOS device produced by German Sympatec GmbH.

The loose bulk density of HPMCAS is preferably from 0.30 to 0.60 g/cm$^3$, more preferably from 0.35 to 0.55 g/cm$^3$, and still more preferably from 0.40 to 0.53 g/cm$^3$, from the viewpoint of handling. The loose bulk density means a bulk density in a loosely packed state. It is measured by a method comprising steps of: uniformly feeding a sample from 23 cm above into a cylindrical container having a volume of 100 mL, a diameter of 5.03 cm and a height of 5.03 cm; then leveling the upper surface of the container; and weighing the container.

The flow rate of HPMCAS in terms of flow through an orifice may be determined by the flow rate measurement, as described in General Information of the Japanese Pharmacopoeia Seventeenth Edition. The flow rate of HPMCAS is preferably from 1.50 to 3.50 g/sec, more preferably from 1.60 to 3.00 g/sec, from the viewpoint of handling. The flow rate extremely greatly depends on the measurement method used as described in General Information of the Japanese Pharmacopoeia Seventeenth Edition. Thus, it is necessary to compare the flow rates measured under the same conditions with each other. Details of the measurement conditions will be described in Examples.

In this specification, HPMCAS particles are divided into four types of particles: "long fibrous particles", "short fibrous particles", "spherical particles" and "fine particles". FIG. 1 shows a flowchart summarizing the method of dividing "all particles" of HPMCAS into four types of particles: "fine particles", "long fibrous particles (LF1 and LF2)", "short fibrous particles (SF1 and SF2)" and "spherical particles (S1 and S2)".

A volume fraction of each type of HPMCAS particles can be calculated by measuring the shape parameters such as a length of fiber (LEFI), a diameter of fiber (DIFI), an elongation, an aspect ratio and a circularity based on a dynamic-image analysis. The dynamic image analysis is a method in which images of particles dispersed in a fluid such as a gas or a solvent are continuously photographed and are binarized and analyzed to obtain a particle diameter or a particle shape. The analysis may be performed by using, for example, a dynamic-image analysis type particle diameter distribution analyzer, QICPIC/R16 (manufactured by Sympatec GmbH).

All particles A are divided into particles C having a length of fiber (LEFI) of 40 µm or more and fine particles B having a length of fiber of less than 40 µm. The LEFI is defined as the length of the longest direct path that connects the ends of the particle within the contour of the particle. A QICPIC/R16 equipped with an M7 lens has a detection limit of 4.7 µm, and thus fails to detect a particle of an LEFI of less than 4.7 µm. However, the volume of the particles having an LEFI of less than 4.7 µm is extremely small relative to that of all particles of HPMCAS, so that it is negligible for the purposes of the invention.

The particles C having an LEFI of 40 µm or more are divided into first spherical particles (S1) having an elongation of 0.5 or more and particles D having an elongation of less than 0.5, wherein the elongation is a ratio (DIFI/LEFI) of a diameter of the fiber (DIFI) to LEF of the particle. The DIFI is defined as the minor diameter of a particle, and is calculated by dividing the projection area of the particle by the sum of all lengths of the fiber branches of the particle.

The particles D having an LEFI of 40 μm or more and an elongation of less than 0.5 are divided into particles E having an aspect ratio of less than 0.5 and particles F having an aspect ratio of 0.5 or more, wherein the aspect ratio is a ratio (Fmin/Fmax) of the minimum Feret diameter (Fmin) to the maximum Feret diameter (Fmax). Each particle has an aspect ratio of more than 0 and not more than 1. The Feret diameter is the distance between two parallel tangent lines that put the particle therebetween. The maximum Feret diameter (Fmax) is the largest distance between pairs of tangent lines to the particle in consideration of all possible orientations by changing the directions from 0° to 180°, and the minimum Feret diameter (Fmin) is a minimum distance between pairs of tangent lines to the particle in consideration of all possible orientations by changing the direction from 0° to 180°.

The fibrous particles E having an LEFI of 40 μm or more, and an elongation of less than 0.5, and an aspect ratio of less than 0.5 are divided into first long fibrous particles (LF1) having an LEFI of 200 μm or more and first short fibrous particles (SF1) having an LEFI of less than 200 μm.

The particles F having an LEFI of 40 μm or more, and an elongation of less than 0.5, and an aspect ratio of 0.5 or more are divided into second spherical particles (S2) having a circularity of 0.7 or more and fibrous particles G having a circularity of less than 0.7. The circularity is a ratio of the perimeter ($P_{EQPC}$) of a circle that has the same area as the projection area ($A_P$) of the particle to the real perimeter ($P_{real}$) of the particle, and is defined by the following equation. Each particle has a circularity of more than 0 and not more than 1. A particle having a smaller circularity has a more irregular shape. The EQPC is the diameter of a circle of an equal projection area, and is defined as the diameter of a circle that has the same area as the projection area of the particle, and is also called Heywood diameter.

$$\text{Circularity} = P_{EQPC}/P_{real} = \sqrt{2\pi A_P}/P_{real}$$

The fibrous particles G having an LEFI of 40 μm or more, an elongation of less than 0.5, an aspect ratio of 0.5 or more, and a circularity of less than 0.7 are divided into second long fibrous particles (LF2) having an LEFI of 200 μm or more and second short fibrous particles (SF2) having an LEFI of less than 200 μm.

The volume ($V_m$) of the fine particles of HPMCAS may be calculated by the following equation where each fine particle is assumed to be a sphere having a diameter of EQPC.

$$V_m = (\pi/6) \times (\text{EQPC})^3 \times N_m,$$

wherein $N_m$ is the number of fine particles in a sample, and EQPC is a median EQPC corresponding to the 50% cumulative value on a number-based cumulative particle diameter distribution curve of fine particles.

In the specification, particles having an LEFI of 40 μm or more, which are particles other than the fine particles having an LEFI of less than 40 μm among all of the particles, are divided into "long fiber particles", "short fiber particles", and "spherical particles", which are distinguished from each other. This division or classification is based the above shape parameters of particles including LEFI, an elongation, an aspect ratio and a circularity.

<Long Fibrous Particles>

Particles satisfying the following definition of LF1 or LF2 are divided into "long fibrous particles".

LF1: particles having an elongation of less than 0.5, an aspect ratio of less than 0.5, and an LEFI (length of fiber) of 200 μm or more, and LF2: particles having an elongation of less than 0.5, an aspect ratio of 0.5 or more, a circularity of less than 0.7, and an LEFI (length of fiber) of 200 μm or more.

The volume ($V_{LF}$) of the long fibrous particles of HPMCAS may be calculated by the following equation wherein each long fibrous particle is assumed to be a cylindrical column having a bottom diameter of DIFI and a height of LEFI.

$$V_{LF} = (\pi/4) \times (\text{DIFI})^2 \times (\text{LEFI}) \times N_{LF},$$

wherein $N_{LF}$ is the number of long fibrous particles in the sample, DIFI is a median DIFI corresponding to the 50% cumulative value on the number-based cumulative particle diameter distribution curve of long fibrous particles, and LEFI is a median LEFI corresponding to the 50% cumulative value on the number-based cumulative particle diameter distribution curve of long fibrous particles.

The volume of particles satisfying the definition of LF1 and the volume of particles satisfying the definition of LF2 are calculated in accordance with the above equation, respectively, and a sum of these volumes means the volume of the long fibrous particles of HPMCAS.

<Short Fibrous Particles>

Particles satisfying the following definition of SF1 or SF2 are divided into "short fibrous particles".

SF1: particles having an elongation of less than 0.5, an aspect ratio of less than 0.5, and an LEFI (length of fiber) of 40 μm or more and less than 200 μm, and SF2: particles having an elongation of less than 0.5, an aspect ratio of 0.5 or more, a circularity of less than 0.7, and an LEFI (length of fiber) of 40 μm or more and less than 200 μm.

The volume ($V_{SF}$) of the short fibrous particles of HPMCAS may be calculated by the following equation where each short fibrous particle is assumed to be a cylindrical column having a bottom diameter of DIFI and a height of LEFI, in the same manner as for the above long fibrous particles.

$$V_{SF} = (\pi/4) \times (\text{DIFI})^2 \times (\text{LEFI}) \times N_{SF},$$

wherein $N_{SF}$ is the number of short fibrous particles in the sample, DIFI is a median DIFI corresponding to the 50% cumulative value on the number-based cumulative particle diameter distribution curve of short fibrous particles, and LEFI is a median LEFI corresponding to the 50% cumulative value on the number-based cumulative particle diameter distribution curve of short fibrous particles.

The volume of particles satisfying the definition of SF1 and the volume of particles satisfying the definition of SF2 are calculated in accordance with the above equation, respectively, and a sum of these volumes means the volume of the short fibrous particles of HPMCAS.

<Spherical Particles>

Particles satisfying the definition S1 or S2 is divided into "spherical particles".

S1: particles having an elongation of 0.5 or more, and an LEFI (length of fiber) of 40 μm or more, and S2: particles having an elongation of less than 0.5, an aspect ratio of 0.5 or more, a circularity of 0.7 or more, and an LEFI (length of fiber) of 40 μm or more.

The volume ($V_S$) of the spherical particles of HPMCAS may be calculated by the following equation, wherein each spherical particle is assumed to be a sphere having a diameter of EQPC.

$$V_S = (\pi/6) \times (\text{EQPC})^3 \times N_S,$$

where $N_S$ is the number of spherical particles in the sample, and EQPC is a median EQPC corresponding to the 50% cumulative value on the number-based cumulative particle diameter distribution curve of spherical particles.

The volume of the particles satisfying the definition S1 and the volume of the particles satisfying the definition S2 are calculated in accordance with the above equation, respectively, and a sum of these volumes means the volume of the spherical particles of HPMCAS.

The volume fraction of each type of particles of HPMCAS may be calculated from the following corresponding equation on basis of the above defined volumes, $V_m$, $V_{LF}$, $V_{SF}$ and $V_S$.

$$\text{Volume fraction of fine particles} = \{V_m/(V_m+V_{LF}+V_{SF}+V_S)\} \times 100$$

$$\text{Volume fraction of long fibrous particles} = \{V_{LF}/(V_m+V_{LF}+V_{SF}+V_S)\} \times 100$$

$$\text{Volume fraction of short fibrous particles} = \{V_{SF}/(V_m+V_{LF}+V_{SF}+V_S)\} \times 100$$

$$\text{Volume fraction of spherical particles} = \{V_S/(V_m+V_{LF}+V_{SF}+V_S)\} \times 100$$

The volume fraction of each type of particles, which are long fibrous particles, short fibrous particles, spherical particles and fine particles, is determined as follows. A dynamic image analysis type particle diameter distribution analyzer QICPIC/R16 (manufactured by Sympatec GmbH) equipped with a quantitative feeder VIBRI/L, an air flow type disperser RODOS/L and an M7 lens is used under the conditions of a frame rate of 500 Hz, an injector of 4 mm, a dispersion pressure of 1 bar. The graphics of the imaged particles are analyzed by analysis software WINDOX5 Version 5.9.1.1 to determine the number-based median EQPC, the number-based median LEFI, the number-based median DIFI, the elongation, the aspect ratio and the circularity with respect to each type of particles. The volume fraction of each type of particles is calculated by the above equation based on the measured values. It is noted that M7 is used as the division of analysis.

The volume fraction of the spherical particles of HPMCAS is 65.0% or more, preferably from 70.0 to 99.0%, and more preferably from 80.0 to 98.0%, from the viewpoint of obtaining HPMCAS excellent in flowability.

The volume fraction of the long fibrous particles of HPMCAS is preferably 30.0% or less, more preferably from 1.0 to 29.5%, and still more preferably from 3.0 to 29.0%, from the viewpoint of flowability of HPMCAS.

The volume fraction of the short fibrous particles of HPMCAS is preferably 2.5% or less, more preferably from 0.0 to 1.5%, and still more preferably from 0.0 to 0.5%, from the viewpoint of flowability of HPMCAS.

The volume fraction of the fine particles of HPMCAS is preferably 2.5% or less, more preferably from 0.0 to 1.5%, and still more preferably from 0.0 to 0.5%, from the viewpoint of flowability of HPMCAS.

Next, there will be described a composition for hot-melt extrusion comprising the above-described hydroxypropyl methyl cellulose acetate succinate and a drug.

By using the above-described HPMCAS having good flowability, the mixing uniformity of HPMCAS and the drug in the composition for hot-melt extrusion, and formation of bridges in the hopper of the mixed powder of HPMCAS and the drug, can be improved. The uniformity of the drug content, the improvement of the mass ratio of HPMCAS to the drug, the quantitative feeding and the continuous operation can also be expected.

The drug is not particularly limited as long as it can be orally administered. Examples of the drug include a drug for the central nervous system, a drug for the cardiovascular system, a drug for the respiratory system, a drug for the digestive system, an antibiotic, an antitussive and expectorant, an antihistamine, an antipyretic anti-inflammatory analgesic, a diuretic, an autonomic agent, an antimalarial agent, an antidiarrheal agent, a psychotropic, and vitamins and derivatives thereof.

Examples of the drug for the central nervous system include diazepam, idebenone, naproxen, piroxicam, indomethacin, sulindac, lorazepam, nitrazepam, phenytoin, acetaminophen (another name: paracetamol), ethenzamide, and chlordiazepoxide.

Examples of the drug for the cardiovascular system include molsidomine, vinpocetine, propranolol, methyldopa, dipyridamole, furosemide, triamterene, nifedipine, atenolol, spironolactone, metoprolol, pindolol, captopril, isosorbide dinitrate, delapril hydrochloride, meclofenoxate hydrochloride, diltiazem hydrochloride, etilefrine hydrochloride, digitoxin, and alprenolol hydrochloride.

Examples of the drug for the respiratory system include amlexanox, dextromethorphan, theophylline, pseudoephedrine, salbutamol, and guaifenesin.

Examples of the drug for the digestive system include a benzimidazole drug having antiulcer action, such as 2-[[3-methyl-4-(2,2,2-trifluoroethoxy)-2-pyridyl]methylsulfinyl] benzimidazole and 5-methoxy-2-[(4-methoxy-3,5-dimethyl-2-pyridyl)methylsulfinyl]benzimidazole; cimetidine; ranitidine; pirenzepine hydrochloride; pancreatin; bisacodyl; and 5-aminosalicylic acid.

Examples of the antibiotic include talampicillin hydrochloride, bacampicillin hydrochloride, cefaclor, and erythromycin.

Examples of the antitussive and expectorant include noscapine hydrochloride, carbetapentane citrate, isoaminile citrate, and dimemorfan phosphate.

Examples of the antihistamine include chlorpheniramine maleate, diphenhydramine hydrochloride, and promethazine hydrochloride.

Examples of the antipyretic anti-inflammatory analgesic include ibuprofen, diclofenac sodium, flufenamic acid, sulpyrine, aspirin, and ketoprofen.

Examples of the diuretic include caffeine.

Examples of the autonomic agent include dihydrocodeine phosphate, dl-methylephedrine hydrochloride, atropine sulfate, acetylcholine chloride, and neostigmine.

Examples of the antimalarial agent include quinine hydrochloride.

Examples of the antidiarrheal agent include loperamide hydrochloride.

Examples of the psychotropic include chlorpromazine.

Examples of the vitamins and derivatives thereof include vitamin A, vitamin B1, fursultiamine, vitamin B2, vitamin B6, vitamin B12, vitamin C, vitamin D, vitamin E, vitamin K, calcium pantothenate, and tranexamic acid.

Particularly using the HPMCAS in accordance with the invention as a carrier of a solid dispersion containing a poorly water-soluble drug, solubility of the poorly water-soluble drug may be improved. Poorly water-soluble drugs refer to drugs listed in the Japanese Pharmacopoeia Seventeenth Edition as "slightly soluble", "very slightly soluble", or "practically insoluble or insoluble" in water. The term "slightly soluble" means that 1 g or 1 mL of a solid pharmaceutical product dissolves in 100 mL or more and less than 1000 mL of water within 30 minutes when placed in a beaker and shaken vigorously at 20±5° C. for 30 seconds every 5 minutes. The term "very slightly soluble" means that 1 g or 1 mL of a solid pharmaceutical product dissolves in 1000 mL or more and less than 10,000 mL of water within 30 minutes in the same manner. The term "practically insoluble or insoluble" means that 1 g or 1 mL of a solid pharmaceutical product dissolves in 10000 mL or more of water within 30 minutes.

In the above test of pharmaceutical product, dissolution of a poorly water-soluble drug means that the drug dissolves or becomes miscible in water, and also means that fibers, etc. are found to be un-present or present at a very slight amount.

Examples of the poorly water-soluble drugs include azole-based compounds such as itraconazole, ketoconazole, fluconazole and methoconazole; dihydropyridine-based compounds such as nifedipine, nitrendipine, amlodipine, nicardipine, nilvadipine, ferrodipine and efonidipine; propionic acid-based compounds such as ibuprofen, ketoprofen and naproxen; indoleacetic acid-based compounds such as indomethacin and acemetacin; griseofulvin; phenytoin; carbamazepine; and dipyridamole.

The mass ratio of HPMCAS to a drug is not particularly limited. It is preferably from 1:0.1 to 1:10, more preferably from 1:0.2 to 1:5, from the viewpoint of storage stability in an amorphous state.

Further, the composition for hot-melt extrusion may comprise an optional additive such as a plasticizer and a surfactant for improving moldability during hot-melt extrusion, or the like.

Examples of the plasticizer include higher alcohols preferably having 10 to 20 carbon atoms, such as cetyl alcohol and stearyl alcohol; polyhydric alcohols preferably having 2 to 6 valences, such as mannitol, sorbitol and glycerin; bead wax; triethyl citrate; polyalkylene glycols such as polyethylene glycol and polypropylene glycol; triacetin; dibutyl sebacete; glycerin monostearate; and monoglycerin acetate.

The content of the plasticizer in the composition for hot-melt extrusion is preferably from 0.1 to 30% by mass from the viewpoint of storage stability.

Examples of the surfactant include an anionic surfactant such as sodium lauryl sulfate; a nonionic surfactant such as diglycerides, poloxamers, polyoxyethylene sorbitan fatty acid esters (Twins 20, 60 and 80), glycerin fatty acid esters and propylene glycol fatty acid esters; and a natural surfactant such as lecithin and sodium taurocholate.

The content of the surfactant in the composition for hot-melt extrusion is preferably from 0.1 to 10% by mass from the viewpoint of storage stability.

The composition for hot-melt extrusion may be prepared by a method comprising a step of mixing HPMCAS, a drug, an optional plasticizer and an optional surfactant to obtain a composition for hot-melt extrusion. The prepared composition for hot-melt extrusion may be introduced into a hot-melt extruder through a hopper, and extruded into a desired shape such as a circular shape, a square shape, a columnar shape or a film to obtain an extrudate.

The hot-melt extruder is not particularly limited as long as it is an extruder capable of melting and kneading HPMCAS and a drug, while heating and applying shear force with a piston or screw, and then extruding them from a die. It is preferably a twin-screw extruder to obtain a more uniform extrudate. Specific examples include Capilograph (single-screw piston type extruder) produced by Toyo Seiki Seisakusho, Ltd.; NANO 16 (twin-screw extruder) produced by Leistritz Extrusionstechnik GmbH; Mini Lab (twin-screw extruder) and Pharma Lab (twin-screw extruder) produced by Thermo Fisher Scientific Inc.

The hot-melt temperature is not particularly limited. It is preferably a temperature at which the composition for hot-melt extrusion is melted and reasonably extruded, while avoiding thermal decompositions of the drug and HPMCAS as much as possible. The hot-melt temperature is preferably from 50 to 250° C., more preferably from 60 to 200° C., and still more preferably from 90 to 190° C., in consideration of the melting points of the drug and HPMCAS as well as the melting point of the composition for hot-melt extrusion.

The conditions for hot-melt extrusion may be appropriately selected depending on the properties of the composition for hot-melt extrusion in accordance with a usual method.

The hot-melt extrudate after extrusion is cooled at the die outlet or later by natural cooling or cold blowing at room temperature (from 1 to 30° C.). The hot-melt extrudate is desirably cooled to 50° C. or less, more preferably 30° C. or less, in order to minimize thermal decomposition of a drug and to suppress recrystallization of an amorphous drug.

The hot-melt extrudate after cooling may be optionally pelletized into pellets of from 0.1 to 5 mm by a cutter, or pulverized into granules or powder for particle size adjustment. An impact mill such as a jet mill, a knife mill or a pin mill is preferably used for the pulverization because it has a structure which hardly raises the product temperature. When the temperature in the cutter and the pulverizer becomes high, HPMCAS is thermally softened and the particles are adhered to each other. Accordingly, pulverization is preferably carried out under cold air blowing.

EXAMPLES

Hereinafter, the invention will be described in detail with reference to Examples and Comparative Example. It should not be construed that the invention is limited by or to them.

In the acetic acid removal step, the concentration of acetic acid in the recovered mixture containing at least the removed acetic acid and water was determined by liquid chromatography under the following conditions.

Equipment: Liquid Chromatograph LC-20AB produced by Shimadzu Corporation.

Column: ODS-3 (inside diameter of 4.6 mm, length of 15 cm, particle size of 5 μm, produced by GL Science Inc.)

Column temperature: 30° C., constant Detector: Ultraviolet-visible absorption photometer (determined at 215 nm, SPD-20AV produced by Shimadzu Corporation)

Mobile phase: A 0.02 mol/L aqueous solution of potassium dihydrogen phosphate, the solution being adjusted to pH 2.8 by addition of phosphoric acid.

Flow rate: 1 mL/min

The measurement sample was prepared by subjecting the recovered mixture containing at least the removed acetic acid and water in the acetic acid removal step to dilution with water by 500 times on a volume basis, and then further to dilution with a mobile phase by 6.25 times on a volume basis.

The flow rate of HPMCAS in terms of flow through an orifice was measured by a flowability tester BEP2 (Copley Scientific Ltd.) under the following conditions to obtain an average value for two measurements.

Orifice size: 8 mm

Feed of HPMCAS: 30 g

Standstill time: 30 seconds

Container: Cylindrical (diameter of 57 mm)

Example 1

The 600 g of HPMC having DS of methoxy groups of 1.88, MS of hydroxypropoxy groups of 0.24 and a viscosity at 20° C. of 3.0 mPa·s as determined in a 2 mass % aqueous solution, 960.0 g of glacial acetic acid, 340.0 g of acetic anhydride, 121.5 g of succinic anhydride and 290.0 g of sodium acetate were placed in a 5 L vertical kneader reactor (Trimix TX-5 produced by INOUE MFG., Ltd.) equipped with three frame-shaped stirring blades which rotate and orbitally revolve; and stirred at 85° C. for 5 hours to obtain 2311.5 g of a reaction product solution containing HPMCAS.

Next, the reaction product solution containing HPMCAS was subjected to addition of 42.0 g of water in the same reactor, while maintaining 85° C., and stirred to obtain 2353.5 g of a water-added reaction product solution. The equivalent relationship in the esterification reaction is shown in Table 1.

TABLE 1

| HPMC (g) | HPMC (mol) | glacial acetic acid (g) | glacial acetic acid (mol/mol HPMC) | acetic anhydride (g) | acetic anhydride (mol/mol HPMC) | succinic anhydride (g) | succinic anhydride (mol/mol HPMC) | sodium acetate (g) | sodium acetate (mol/mol HPMC) |
|---|---|---|---|---|---|---|---|---|---|
| 600.0 | 3.0 | 960.0 | 5.4 | 340.0 | 1.1 | 121.5 | 0.4 | 290.0 | 1.2 |

Subsequently, the internal pressure in the same kneader reactor was reduced to −0.09 MPaG by using an aspirator (A-1000S produced by Tokyo Rika-Kikai Co., Ltd.), and stirred at 85° C. for 30 minutes to recover acetic acid into an ice-cooled trap. The recovered acetic acid contained water, and the amount of the recovered mixture containing at least acetic acid and water was 156.0 g. Then, by cooling the inside of the kneader reactor to room temperature, there was obtained a sticky solid-like mixture containing HPMCAS and having the acetic acid content reduced.

The peripheral speed in the rotational motion of each frame-shaped stirring blade in the esterification step, the water addition step and the acetic acid removal step was 0.050 m/s, the peripheral speed in the revolving motion was 0.019 m/s. The ratio of the peripheral speed in the rotational motion to the peripheral speed in the revolving motion was 2.6. Further, the peripheral speeds in the rotational motion were the same between all of the three frame-shaped stirring blades which rotated and orbitally revolved.

Next, 100 parts by mass of the sticky solid-like mixture was subjected to addition of 300 parts by mass of water of 20° C., and pulverized at a rotational speed of 8000 rpm and a peripheral speed of 12.57 m/sec in a homogenizing mixer (Homomixer MARK II 2.5 produced by PRIMIX Corporation; rotor diameter of 30.0 mm) to obtain a suspension of the pulverized mixture. Then, the pulverized mixture was filtered to obtain crude HPMCAS.

Thereafter, a sequence of dispersing the crude HPMCAS in water, stirring and filtering was repeated 10 times for washing to obtain washed HPMCAS. The temperature of water used for washing was 20° C., and the amount of water used in each sequence for washing was 500 parts by mass relative to 100 parts by mass of the solid-like mixture having the acetic acid content reduced. The washed HPMCAS was dried for 2 hours at a temperature of 80° C., and sieved through a sieve having an opening of 0.5 mm to obtain HPMCAS.

Table 2 shows a mass ratio (A) of the glacial acetic acid used as a solvent to HPMC, a mass ratio (B) of water added in the water addition step after completion of the esterification step to HPMC, a mass ratio (C) of a recovered mixture containing at least acetic acid and water in the acetic acid removal step to HPMC, a concentration (D) of acetic acid in a recovered mixture containing at least acetic acid and water, a removal percentage of acetic acid, and a form of the mixture having the acetic acid content reduced before subjected to the washing and recovery step. Table 3 shows various properties of the obtained HPMCAS.

Example 2

A non-sticky solid-like mixture containing HPMCAS and having the acetic acid content reduced was obtained in the same manner as in Example 1 except that the stirring time in the acetic acid removal step was 60 minutes and an amount of the recovered mixture containing at least the removed acetic acid and water was 884.0 g.

Next, the solid-like mixture having the acetic acid content reduced was pulverized at a rotational speed of 4000 rpm and a peripheral speed of 55.79 m/s in Feather Mill FM-1F (produced by Hosokawa Micron Corporation; a rotor diameter of 266.4 mm) equipped with a knife-type milling blade and a screen having an opening of 0.8 mm. Then, 100 parts by mass of the pulverized mixture having the acetic acid content reduced was subjected to addition of 300 parts by mass of water of 20° C., and mixed to obtain the water-containing mixture of the pulverized mixture and water. The water-containing mixture was filtered to obtain crude HPMCAS.

Thereafter, a sequence of dispersing the crude HPMCAS in water, stirring and filtering was repeated 10 times for washing to obtain washed HPMCAS. The temperature of water used for washing was 20° C., and the amount of water used in each sequence for washing was 500 parts by mass relative to 100 parts by mass of the solid-like mixture having the acetic acid content reduced. Thereafter, the washed HPMCAS was dried, and sieved in the same manner as in Example 1 to obtain HPMCAS. The results are shown in Tables 2 and 3.

Example 3

HPMCAS was obtained in the same manner as in Example 1 except that an amount of water added to the reaction product solution containing HPMCAS was 676.0 g, the stirring time in the acetic acid removal step was 50 minutes, and an amount of the recovered mixture containing at least acetic acid and water was 684.0 g. It is noted that a sticky solid-like mixture containing HPMCAS and having the acetic acid content reduced was obtained in the acetic acid removal step. The results are shown in Tables 2 and 3.

Example 4

HPMCAS was obtained in the same manner as in Example 1 except that an amount of water added to the reaction product solution containing HPMCAS was 676.0 g, the stirring time in the acetic acid removal step was 80 minutes, and an amount of the recovered mixture containing at least acetic acid and water was 819.3 g. It is noted that a sticky solid-like mixture containing HPMCAS and having the acetic acid content reduced was obtained in the acetic acid removal step. The results are shown in Tables 2 and 3.

Example 5

HPMCAS was obtained in the same manner as in Example 2 except that an amount of water added to the reaction product solution containing HPMCAS was 676.0 g, the stirring time in the acetic acid removal step was 120 minutes, and an amount of the recovered mixture containing at least acetic acid and water was 1548.0 g. It is noted that a non-sticky solid-like mixture containing HPMCAS and having the acetic acid content reduced was obtained in the acetic acid removal step. The results are shown in Tables 2 and 3.

Comparative Example 1

HPMCAS was obtained in the same manner as in Example 1 except that an amount of water added to the reaction product solution containing HPMCAS was 676.0 g, and the water-added reaction product solution was placed in a homogenized mixer in the absence of the acetic acid removal step. The results are shown in Tables 2 and 3.

TABLE 2

| | mass ratio (A) of glacial acetic acid as solvent to HPMC | mass ratio (B) of water added in water addition step to HPMC | mass ratio (C) of recovered mixture containing acetic acid to HPMC | conc. (D) of acetic acid in recovered mixture (mass %) | removal percentage of acetic acid (%) | form of the mixture having acetic acid content reduced |
|---|---|---|---|---|---|---|
| Example1 | 1.60 | 0.07 | 0.26 | 95.7 | 15.6 | solid |
| Example2 | 1.60 | 0.07 | 1.47 | 97.4 | 89.5 | solid |
| Example3 | 1.60 | 1.13 | 1.14 | 46.3 | 33.0 | solid |
| Example4 | 1.60 | 1.13 | 1.37 | 55.0 | 47.1 | solid |
| Example5 | 1.60 | 1.13 | 2.58 | 61.9 | 99.8 | solid |
| Comp. Ex. 1 | 1.60 | 1.13 | 0.00 | — | — | liquid |

TABLE 3

| | viscosity (mPa·s) | MeO | HPO | Ac | Suc | Ac/Su | $D_{50}$ (μm) | particle size ratio of $D_{90}$ to $D_{10}$ |
|---|---|---|---|---|---|---|---|---|
| Example1 | 2.7 | 1.90 | 0.24 | 0.57 | 0.30 | 1.91 | 342 | 3.26 |
| Example2 | 2.7 | 1.89 | 0.24 | 0.55 | 0.30 | 1.85 | 323 | 2.57 |
| Example3 | 2.7 | 1.89 | 0.24 | 0.55 | 0.30 | 1.85 | 422 | 2.82 |
| Example4 | 2.7 | 1.89 | 0.24 | 0.55 | 0.30 | 1.85 | 488 | 2.79 |
| Example5 | 2.7 | 1.87 | 0.24 | 0.52 | 0.28 | 1.86 | 358 | 3.15 |
| Comp. Ex. 1 | 2.7 | 1.87 | 0.24 | 0.52 | 0.28 | 1.86 | 511 | 4.13 |

| | loose bulk density (g/cm³) | flow rate (g/sec) | spherical particles (%) | long fibrous particles (%) | short fibrous particles (%) | fine particles (%) |
|---|---|---|---|---|---|---|
| Example1 | 0.305 | 1.656 | 78.8 | 20.9 | 0.2 | 0.1 |
| Example2 | 0.352 | 2.449 | 95.4 | 4.5 | 0.0 | 0.1 |
| Example3 | 0.420 | 1.612 | 70.9 | 28.8 | 0.2 | 0.1 |
| Example4 | 0.449 | 1.678 | 81.8 | 18.2 | 0.0 | 0.0 |
| Example5 | 0.498 | 2.440 | 93.2 | 6.7 | 0.1 | 0.0 |
| Comp. Ex. 1 | 0.292 | 1.401 | 12.8 | 86.6 | 0.5 | 0.1 |

*1 "viscosity" means the viscosity at 20° C. of a 2% by mass solution of HPMCAS in an 43% by mass NaOH aqueous solution, "MeO" means methoxy groups, "HPO" means hydroxypropoxy groups, "Ac" means acetyl groups, and "Suc" means succinyl groups.

By carrying out the acetic acid removal step, there was obtained HPMCAS having a volume fraction of spherical particles of 65.0% or more. A good particle size ratio of $D_{90}$ to $D_{10}$, a good loose bulk density, and a good flow rate were exhibited. In addition, cost reduction can be expected by reducing the burden in wastewater treatment and reusing the recovered acetic acid. Further, the mixing uniformity of HPMCAS and a drug in the composition for hot-melt extrusion, and the formation of bridges in the hopper of the mixed powder of HPMCAS and the drug can be improved. Uniformity of the drug content, the improvement of the mass ratio of HPMCAS to the drug, quantitative supply and continuous operation can be expected.

The invention claimed is:

1. A method for producing hydroxypropyl methyl cellulose acetate succinate comprising:
   an esterification step of esterifying hydroxypropyl methyl cellulose with acetic anhydride and succinic anhydride in acetic acid as a solvent to obtain a reaction product solution containing hydroxypropyl methylcellulose acetate succinate;
   a water addition step of adding water to the reaction product solution to obtain a water-added reaction product solution;
   an acetic acid removal step of removing at least a portion of both the solvent acetic acid and acetic acid derived from the acetic anhydride from the water-added reaction product solution to obtain a mixture having an acetic acid content reduced; and
   a wash and recovery step of washing the mixture and recovering the hydroxypropyl methyl cellulose acetate succinate.

2. The method for producing hydroxypropyl methyl cellulose acetate succinate according to claim 1, wherein an amount of the acetic acid removed in the acetic acid removal step corresponds to 10.0% or more of the solvent acetic acid.

3. The method for producing hydroxypropyl methyl cellulose acetate succinate according to claim 1, wherein the acetic acid removal step comprises evaporating the acetic acid by heating and stirring the water-added reaction product solution under a reduced pressure.

4. The method for producing hydroxypropyl methyl cellulose acetate succinate according to claim 2, wherein the acetic acid removal step comprises evaporating the acetic acid by heating and stirring the water-added reaction product solution under a reduced pressure.

* * * * *

UNITED STATES PATENT AND TRADEMARK OFFICE
CERTIFICATE OF CORRECTION

PATENT NO. : 11,767,371 B2  
APPLICATION NO. : 17/484405  
DATED : September 26, 2023  
INVENTOR(S) : Miki et al.

Page 1 of 1

It is certified that error appears in the above-identified patent and that said Letters Patent is hereby corrected as shown below:

In the Specification

Column 9, Line 39: Please remove the formula and replace with the following:

$$\text{Circularity} = P_{EQPC}/P_{real} = 2\sqrt{\pi \cdot A_p}\,/P_{real}$$

Column 14, Line 47: Please insert a paragraph break between "constant" and "Detector:"

Signed and Sealed this  
Fifteenth Day of April, 2025

Coke Morgan Stewart  
*Acting Director of the United States Patent and Trademark Office*